US009393438B2

(12) United States Patent
Witt et al.

(10) Patent No.: US 9,393,438 B2
(45) Date of Patent: Jul. 19, 2016

(54) SYSTEM AND METHOD FOR ADMINISTERING LIGHT THERAPY

(75) Inventors: Erik Kurt Witt, Murrysville, PA (US); Mark Toddman Kirby, Spring Church, PA (US); Michael Edward Colbaugh, Level Green, PA (US)

(73) Assignee: Koninklijke Philips N.V., Eindhoven (NL)

( * ) Notice: Subject to any disclaimer, the term of this patent is extended or adjusted under 35 U.S.C. 154(b) by 672 days.

(21) Appl. No.: 13/142,859

(22) PCT Filed: Dec. 9, 2009

(86) PCT No.: PCT/IB2009/055620
§ 371 (c)(1),
(2), (4) Date: Sep. 8, 2011

(87) PCT Pub. No.: WO2010/076709
PCT Pub. Date: Jul. 8, 2010

(65) Prior Publication Data
US 2012/0209355 A1 Aug. 16, 2012

Related U.S. Application Data

(60) Provisional application No. 61/141,292, filed on Dec. 30, 2008.

(51) Int. Cl.
*A61N 5/06* (2006.01)
*A61M 21/00* (2006.01)
*A61M 21/02* (2006.01)

(52) U.S. Cl.
CPC ............. *A61N 5/0618* (2013.01); *A61M 21/00* (2013.01); *A61M 21/02* (2013.01);
(Continued)

(58) Field of Classification Search
CPC .................... A61N 5/0618; A61N 2005/0648; A61M 21/00; A61M 21/02; A61M 2205/3306; A61M 2205/3569; A61M 2205/3592; A61M 2205/502; A61M 2230/10; A61M 2230/18; A61M 2230/50
USPC ...................................... 607/88–94
See application file for complete search history.

(56) References Cited

U.S. PATENT DOCUMENTS

| 5,507,716 A | 4/1996 | LaBerge et al. |
| 6,053,936 A * | 4/2000 | Koyama et al. ............... 607/88 |

(Continued)

FOREIGN PATENT DOCUMENTS

| DE | 3823402 A1 | 1/1990 |
| EP | 1982747 A1 | 10/2008 |

(Continued)

OTHER PUBLICATIONS

HTTPS://www.lowbuelights.com, Bright-Eye Yellow Eyeglasses for Blocking-Out Blue and UV Light, Downloaded May 22, 2014, 5 Pages.

(Continued)

*Primary Examiner* — Ahmed Farah
*Assistant Examiner* — Boniface Nganga

(57) ABSTRACT

A sleep mask is configured to provide light therapy to a subject. The sleep mask may provide a comfortable delivery mechanism for the light therapy, and may deliver the light therapy to the subject while the subject is asleep, in the process of going to sleep, and/or waking from sleep. In one embodiment, the sleep mask includes one or more of a shield, a strap, a first lighting module, and/or a second lighting module.

12 Claims, 5 Drawing Sheets

(52) U.S. Cl.
CPC ............... *A61M 2021/0044* (2013.01); *A61M 2205/3306* (2013.01); *A61M 2205/3569* (2013.01); *A61M 2205/3592* (2013.01); *A61M 2205/502* (2013.01); *A61M 2230/10* (2013.01); *A61M 2230/18* (2013.01); *A61M 2230/50* (2013.01); *A61N 2005/0648* (2013.01)

(56) References Cited

U.S. PATENT DOCUMENTS

| | | | |
|---|---|---|---|
| 6,092,906 A | 7/2000 | Olmstead | |
| 2004/0163648 A1* | 8/2004 | Burton | 128/204.21 |
| 2008/0234785 A1* | 9/2008 | Nakayama et al. | 607/62 |

FOREIGN PATENT DOCUMENTS

| | | |
|---|---|---|
| JP | S59211463 A | 11/1984 |
| JP | 07042999 A | 2/1995 |
| JP | 2007098138 A | 4/2007 |
| JP | 2007228003 A | 9/2007 |
| JP | 2008086489 A | 4/2008 |

OTHER PUBLICATIONS

HTTP://www.flightgear.dk/flash.htm, Flightgear On-Line, Downloaded May 30, 2014, 6 Pages.

HTTP://en.wikipedia.org/wiki/rear-view_mirror, Downloaded May 30, 2014, 3 Pages.

HTTP://en.wikipedia.org/wiki/electrochromism, Downloaded May 30, 2014, 3 Pages.

* cited by examiner

SYSTEM AND METHOD FOR ADMINISTERING LIGHT THERAPY

CROSS REFERENCE TO RELATED APPLICATIONS

This application claims the benefit of U.S. provisional application Ser. No. 61/141,292 filed Dec. 30, 2008, which is incorporated herein by reference.

This application is related to U.S. Patent Application Ser. No. 61/141,273, entitled "SYSTEM AND METHOD FOR PROVIDING LIGHT THERAPY TO A SUBJECT," and filed Dec. 30, 2008, and U.S. Patent Application Ser. No. 61/141,274 entitled "SYSTEM AND METHOD FOR PROVIDING LIGHT THERAPY TO A SUBJECT," and filed Dec. 30, 2008, and U.S. Patent Application Ser. No. 61/141,289 entitled "SYSTEM AND METHOD FOR ADMINISTERING LIGHT THERAPY," filed Dec. 30, 2008, and U.S. Patent Application Ser. No. 61/141,295 entitled "SYSTEM AND METHOD FOR ADMINISTERING LIGHT THERAPY," filed Dec. 30, 2008, and U.S. Patent Application Ser. No. 61/152,028 entitled "SYSTEM AND METHOD FOR PROVIDING LIGHT THERAPY TO A SUBJECT," filed Feb. 12, 2009, which are hereby incorporated into this application in its entirety.

The invention relates to the administration of light therapy to a subject.

The direction of radiation on a subject to impact the Circadian rhythms and/or to address light deficient disorders of the subject are known. Generally, these treatments involve shining light directly towards a patient's eyes while the patient is awake to alleviate or cure light deficient disorders including Seasonal Affective Disorder (SAD), circadian sleep disorders and circadian disruptions associated with jet-lag, and shift-work.

There are two types of light therapy devices presently available. One type of device is large in size and floor or desk mountable. These devices include light sources of fluorescent bulbs or large arrays of light emitting diodes. Although they can be moved from one position to another, they are not generally portable and require a scheduled time period of being stationary during the active part of the day. In addition, the light source is quite fragile. The second kind of light therapy device is head mountable. These devices are formed as eyeglasses or visors. While they are portable, they are not generally accepted by patients for use in public because of their odd appearance when worn on the head. These devices generally lack features that enable them to be used while functioning during sleep. This second type of device mostly used focused or non-diffuse light sources to direct high luminance light towards the eyes.

Further, the lights are positioned to emit beams of light at the eyes of the patient while the patient is awake. This approach may impact the comfort of the treatment to the subject.

One aspect of the invention relates to a system configured to provide light therapy to a subject as the subject sleeps. In one embodiment, the system comprises one or more lighting modules, one or more sensors, and a processor. The one or more lighting modules are configured to provide radiation to the eyes of the subject. The one or more sensors are configured to generate one or more output signals that convey information related to the position of the eyelids of the subject. The processor is configured to receive the one or more output signals generated by the one or more sensors, and to control the one or more lighting modules such that the one or more lighting modules provide radiation to the eyes of the subject at an intensity level that is determined based on the position of the eyelids of the subject.

Another aspect of the invention relates to a method of providing light therapy to a subject as the subject sleeps. In one embodiment, the method comprises providing radiation to the eyes of the subject at a first intensity; determining information related to the position of the eyelids of the subject; and adjusting the intensity of the radiation provided to the eyes of the subject based on the position of the eyelids of the subject.

Another aspect of the invention relates to a system configured to provide light therapy to a subject as the subject sleeps. In one embodiment, the system comprises means for providing radiation to the eyes of the subject at a first intensity; means for adjusting the intensity of the radiation provided to the eyes of the subject based on the position of the eyelids of the subject; and means for adjusting the intensity of the radiation provided to the eyes of the subject based on the position of the eyelids of the subject.

Another aspect of the invention relates to a system configured to provide light therapy to a subject as the subject sleeps. In one embodiment, the system comprises one or more lighting modules, one or more sensors, and a processor. The one or more lighting modules are configured to provide radiation to the eyes of the subject. The one or more sensors are configured to generate one or more output signals that convey information about the current sleep stage of the subject. The processor is configured to control the one or more lighting modules such that the one or more lighting modules provide radiation to the eyes of the subject, wherein the processor varies causes the intensity of the light provided to the eyes of the subject by the one or more lighting modules to vary based on the one or more output signals that convey information about the current sleep stage of the subject.

Another aspect of the invention relates to a method of providing light therapy to a subject as the subject sleeps. In one embodiment, the method comprises providing radiation to the eyes of the subject; determining the current sleep stage of the subject; and adjusting the intensity of the radiation directed to the eyes of the subject based on the current sleep stage of the subject.

Another aspect of the invention relates to a system configured to provide light therapy to a subject as the subject sleeps. In one embodiment, the system comprises means for providing radiation to the eyes of the subject; means for determining the current sleep stage of the subject; and means for adjusting the intensity of the radiation directed to the eyes of the subject based on the current sleep stage of the subject.

Another aspect of the invention relates to a system configured to provide light therapy to a subject. In one embodiment, the system comprises one or more lighting modules and a processor. The one or more lighting modules are configured to administer visible radiation to the subject, wherein the radiation administered to the subject comprises a first portion of the visible radiation and a second portion of the visible radiation, the first portion of the visible radiation having wavelengths that fall within a first section of the visible spectrum and the second portion of the visible radiation having wavelengths that are within the visible spectrum but outside of the first section of the visible spectrum. The processor is configured to control the one or more lighting modules such that the first portion of the visible radiation and the intensity of the second portion of the visible radiation over time such that the overall intensity of the administered visible radiation remains relatively fixed.

Another aspect of the invention relates to a method of providing light therapy to a subject. In one embodiment, the method comprises administering visible radiation to the subject, wherein the radiation administered to the subject comprises a first portion of the visible radiation and a second portion of the visible radiation, the first portion of the visible radiation having wavelengths that fall within a first section of the visible spectrum and the second portion of the visible radiation having wavelengths that are within the visible spectrum but outside of the first section of the visible spectrum; and varying the intensity of the first portion of the visible radiation and the intensity of the second portion of the visible radiation over time such that the overall intensity of the administered visible radiation remains relatively fixed.

Another aspect of the invention relates to a system configured to provide light therapy to a subject. In one embodiment, the system comprises means for administering visible radiation to the subject, wherein the radiation administered to the subject comprises a first portion of the visible radiation and a second portion of the visible radiation, the first portion of the visible radiation having wavelengths that fall within a first section of the visible spectrum and the second portion of the visible radiation having wavelengths that are within the visible spectrum but outside of the first section of the visible spectrum; and means for varying the intensity of the first portion of the visible radiation and the intensity of the second portion of the visible radiation over time such that the overall intensity of the administered visible radiation remains relatively fixed.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. As used in the specification and in the claims, the singular form of "a", "an", and "the" include plural referents unless the context clearly dictates otherwise.

Figure 1:
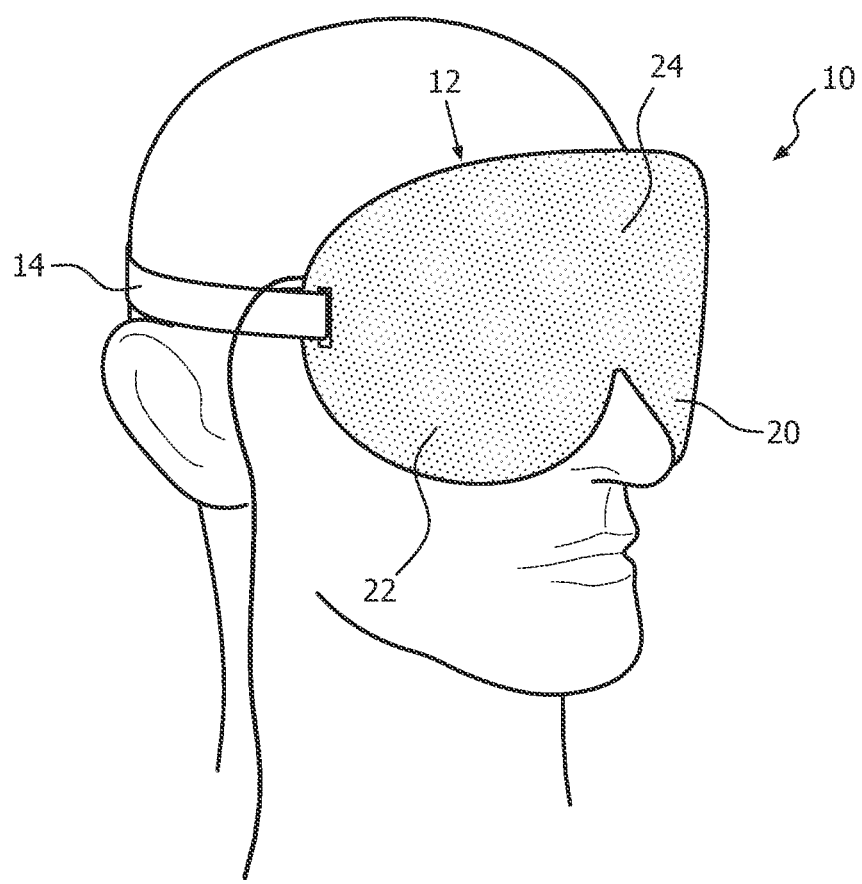
FIG. 1 illustrates a sleep mask configured to provide light therapy to a subject, in accordance with one embodiment of the invention.
Figure 2:
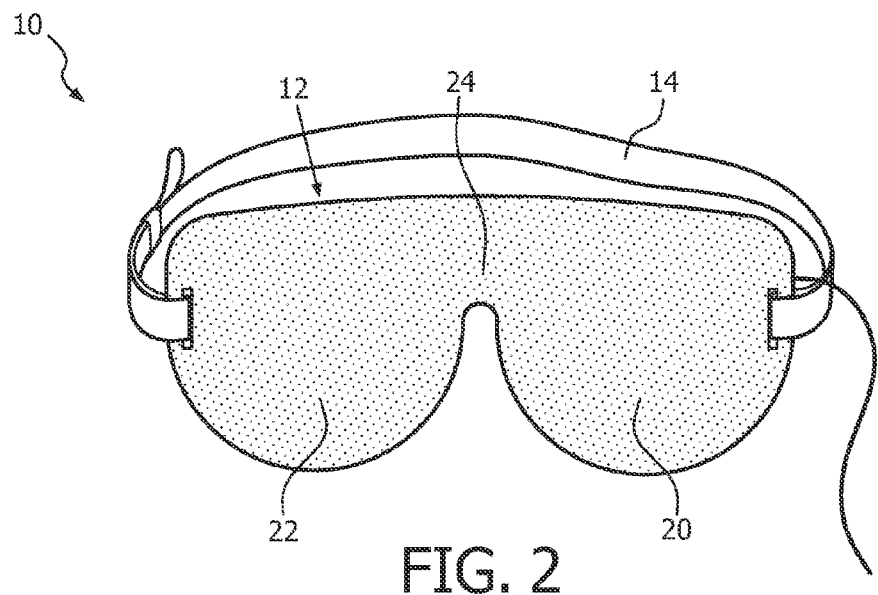
FIG. 2 illustrates a sleep mask configured to provide light therapy to a subject, in accordance with one embodiment of the invention.
Figure 3:
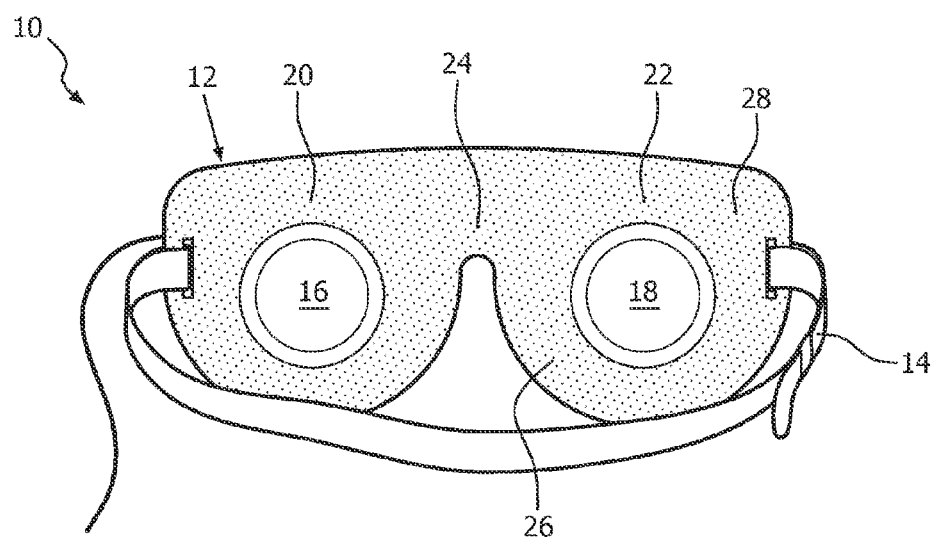
FIG. 3 illustrates a sleep mask configured to provide light therapy to a subject, in accordance with one embodiment of the invention.

FIGS. 1-3 illustrate a sleep mask 10 configured to provide light therapy to a subject. Sleep mask 10 may provide a comfortable delivery mechanism for the light therapy, and may deliver the light therapy to the subject while the subject is asleep, in the process of going to sleep, and/or waking from sleep. In one embodiment, sleep mask 10 includes one or more of a shield 12, a strap 14, a first lighting module 16, and/or a second lighting module 18.

As can be seen in FIG. 1, shield 12 is configured to cover the eyes of the subject wearing sleep mask 10. In one embodiment, shield 12 includes a first shield portion 20 and a second shield portion 22. First shield portion 20 is configured to cover a first eye of the subject. Second shield portion 22 is configured to cover a second eye of the subject. In order to comfortably cover the first eye and the second eye of the subject, first shield portion 20 and second shield portion 22 are substantially larger than the ocular openings of the eyes of the subject.

In one embodiment, first shield portion 20 and second shield portion 22 are joined by a connecting shield portion 24. Connecting shield portion 24 is configured to rest on at least a portion of the nose of the subject (e.g., across the bridge of the nose) when the subject is wearing sleep mask 10. In some instances (not shown), connecting shield portion 24 may be narrower or thicker than the embodiment depicted in FIGS. 1-3.

In one embodiment, shield 12 is formed from flexible materials. The flexibility of shield 12 may enhance the comfort of shield 12 to the subject. The side of shield 12 visible in FIG. 3 faces toward the subject during use. On this side, a base surface 26 substantially impermeable to liquids may be formed. For example, the impermeable base surface 26 may be formed by a flexible plastic material such as polycarbonate, polyester, and/or other materials. The impermeability of base surface 26 may protect electronic components of sleep mask 10 carried within shield 12 from moisture.

In one embodiment, shield 12 includes a cushioning layer 28 disposed on base surface 26. Cushioning layer 28 is formed from a soft, resilient material. For example, cushioning layer 28 may be formed from foam, foam, fabric/foam laminate, and/or other materials. During use, cushioning layer 28 provides the innermost surface to the subject, and engages the face of the subject. As such, the softness of cushioning layer 28 provides a cushion for the face of the subject, and enhances the comfort of sleep mask 10 to the subject.

As will be appreciated from the foregoing and FIGS. 1-3, during use shield 12 provides a barrier between ambient radiation and the eyes of the subject. In one embodiment, shield 12 is opaque, and blocks ambient radiation (at least within the visible spectrum), thereby shielding the eyes of the subject from ambient radiation.

Strap 14 is configured to hold shield 12 in place on the subject. In the embodiments shown in FIGS. 1-3, strap 14 is attached to each of first shield portion 20 and second shield portion 22, and wraps around the head of the subject to hold sleep mask 10 in place on the head of the subject. Strap 14 may be adjustable in length (e.g., to accommodate different sized heads). Strap 14 may be formed from a resilient material (e.g., elastic) that stretches to accommodate the head of the user and holds shield 12 in place. It should be appreciated that the inclusion of strap 14 in the embodiments of sleep mask 10 illustrated in FIGS. 1-3 is not intended to be limiting. Other mechanisms for holding shield 12 in place on the subject are contemplated. For example, a more elaborate headgear may be implemented, an adhesive surface may be applied to shield 12 that removably adheres to the skin of the subject to hold shield 12 in place, and/or other mechanisms for holding shield 12 in place may be implemented.

Referring now to FIG. 3, first lighting module 16 and second lighting module 18 are mounted to first shield portion 20 and second shield portion 22, respectively, on the side of shield 12 that faces toward the face of the subject during use. First lighting module 16 and second lighting module 18 are backlit, and are configured to emit radiation onto the face of the subject on and/or about the eyes of the subject. The radiation emitted by first lighting module 16 and second lighting module 18 has a wavelength (or wavelengths) that have a therapeutic impact on the subject, when they are delivered in accordance with an effective light therapy plan. In some instances, the radiation emitted by first lighting module 16 and second lighting module 18 is directed towards the eyes of the subject in radiation fields having relatively uniform luminance as perceived by the subject. For example, in one embodiment, the luminance of the radiation emitted by first lighting module 16 and second lighting module 18 varies across the respective emitted fields by an amount that is less than or equal to about 100:1 for use with eyes open, and less than 10,000:1 for eyes-closed applications. The size of the uniform field of radiation formed by either first lighting module 16 or second lighting module 18 may correspond to the size of the eye of the subject.

Figure 4:
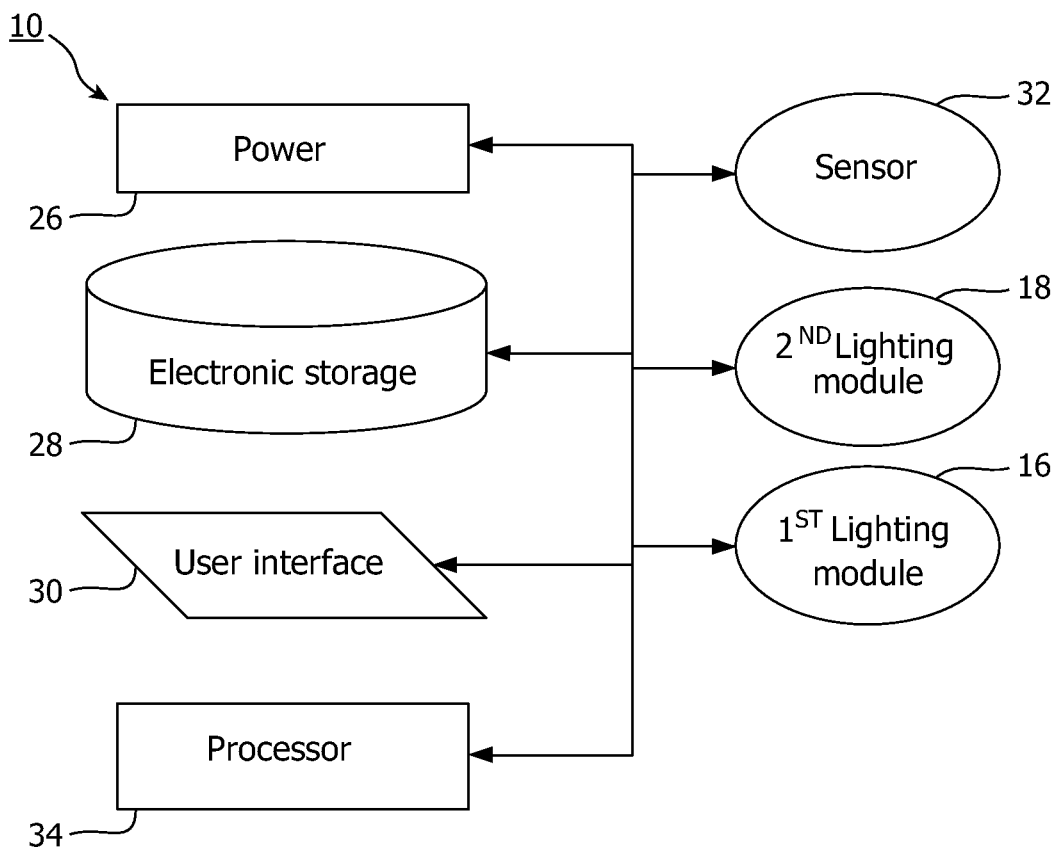
FIG. 4 illustrates a schematic representation of a sleep mask configured to provide light therapy to a subject, in accordance with one embodiment of the invention.

FIG. 4 is a schematic illustration of sleep mask 10, in accordance with one or more embodiments of the invention. As can be seen in FIG. 4, in addition to one or more of the components shown in FIGS. 1-3 and described above, sleep mask 10 may include one or both of a power source 26, electronic storage 28, a user interface 30, one or more sensors 32, and/or a processor 34. In one embodiment, one or more of power source 26, electronic storage 28, user interface 30, one or more sensors 32, and/or processor 34 are carried on shield 12 and/or strap 14 of sleep mask 10. In this embodiment, one or more of power source 26, electronic storage 28, user interface 30, one or more sensors 32 and/or processor 34 may be removably attached to shield 12 and/or strap 14, and may be disconnectable from the rest of sleep mask 10. This will enable power source 26, electronic storage 28, user interface 30, one or more sensors 32 and/or processor 34 to be removed from a given shield 12 and/or strap 14, and attached to another shield 12 and/or strap 14, which may be beneficial if shield 12 and/or strap 14 degrade over time and/or with usage and must be replaced. Similarly, in one embodiment, first lighting module 16 and second lighting module 18 are also removable/replaceable on shield 12. Power source 26, electronic storage 28, user interface 30, one or more sensors 32 and/or processor 34 may control operation the radiation sources associated with first lighting module 16 and/or second lighting module 18, as is discussed below.

Power source 26 provides the power necessary to operation the radiation sources associated with first lighting module 16 and second lighting module 18, and/or to power electronic storage 28, user interface 30, and/or processor 34. Power source 26 may include a portable source of power (e.g., a battery, a fuel cell, etc.), and/or a non-portable source of power (e.g., a wall socket, a large generator, etc.). In one embodiment, power source 26 includes a portable power source that is rechargeable. In one embodiment, power source 26 includes both a portable and non-portable source of power, and the subject is able to select which source of power should be used to provide power to sleep mask 10.

In one embodiment, electronic storage 28 comprises electronic storage media that electronically stores information. The electronically storage media of electronic storage 28 may include one or both of system storage that is provided integrally (i.e., substantially non-removable) with sleep mask 10 and/or removable storage that is removably connectable to sleep mask 10 via, for example, a port (e.g., a USB port, a firewire port, etc.) or a drive (e.g., a disk drive, etc.). Electronic storage 28 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 28 may store software algorithms, information determined by processor 34, information received via user interface 30, and/or other information that enables sleep mask 10 to function properly. Electronic storage 28 may include media provided as a separate component within sleep mask 10. Electronic storage 28 may include media provided integrally with one or more other components of sleep mask 10 (e.g., processor 34).

User interface 30 is configured to provide an interface between sleep mask 10 and the subject (and/or a caregiver) through which the subject (and/or a caregiver) may provide information to and receive information from sleep mask 10. This enables data, results, and/or instructions and any other communicable items, collectively referred to as "information," to be communicated between the subject and processor 34. Examples of interface devices suitable for inclusion in user interface 30 include a keypad, buttons, switches, a keyboard, knobs, levers, a display screen, a touch screen, speakers, a microphone, an indicator light, an audible alarm, and a printer. In one embodiment, the functionality of which is discussed further below, user interface 30 actually includes a plurality of separate interfaces, including one interface that is carried on sleep mask 10, and a separate interface provided to view and/or manage stored information that has been retrieved from sleep mask 10 (e.g., provided by a host computer to which information from sleep mask 10 can be received).

It is to be understood that other communication techniques, either hard-wired or wireless, are also contemplated by the present invention as user interface 30. For example, the present invention contemplates that user interface 30 may be integrated with a removable storage interface provided by electronic storage 28. In this example, information may be loaded into sleep mask 10 from removable storage (e.g., a smart card, a flash drive, a removable disk, etc.) that enables the user(s) to customize the implementation of sleep mask 10. Other exemplary input devices and techniques adapted for use with sleep mask 10 as user interface 30 include, but are not limited to, an RS-232 port, RF link, an IR link, modem (telephone, cable or other). In short, any technique for communicating information with sleep mask 10 is contemplated by the present invention as user interface 30.

One or more sensors 32 are configured to generate one or more output signals that convey information about the current sleep stage of the subject. In one embodiment, the current sleep stage of the subject may be determined from the one or more output signals generated by one or more sensors 32. Determining the current sleep stage of the subject may include determining if the subject is in REM sleep or non-REM sleep. Determining the current sleep stage of the subject may include determining if the subject is in stage 1 sleep, stage 2 sleep, or stage 3 sleep. In one embodiment, one or more sensors 32 include one or more of a sensor configured to generate an output signal that indicates a distance between the eye of the subject and the sensor, a sensor configured to generate an output signal that indicates a core body temperature, an EEG sensor, and/or other sensors.

Processor 34 is configured to provide information processing and/or system control capabilities in sleep mask 10. As such, processor 34 may include one or more of a digital processor, an analog processor, a digital circuit designed to process information, an analog circuit designed to process information, a state machine, and/or other mechanisms for electronically processing information. In order to provide the functionality attributed to processor 34 herein, processor 34 may execute one or more modules. The one or more modules may be implemented in software; hardware; firmware; some combination of software, hardware, and/or firmware; and/or otherwise implemented. Although processor 34 is shown in FIG. 1 as a single entity, this is for illustrative purposes only. In some implementations, processor 34 may include a plurality of processing units. These processing units may be physically located within the same device (e.g., sleep mask 10), or processor 34 may represent processing functionality of a plurality of devices operating in coordination.

In one embodiment, processor 34 controls first lighting module 16 and second lighting module 18 in accordance with a predetermined light therapy algorithm. The predetermined light therapy algorithm may dictate the timing, the intensity, and/or the wavelength of the radiation emitted by first lighting module 16 and second lighting module 18 toward the face of the subject on or about the eyes of the subject. In one embodiment, the predetermined light therapy algorithm is stored in electronic storage 28, and is provided to processor 34 for execution via control of first lighting module 16 and second lighting module 18. In some instances, one or more aspects of the predetermined light therapy algorithm may be adjusted or customized for the subject. Adjustments and/or customizations to the predetermined light therapy algorithm may be input to sleep mask 10 via user interface 30. In one embodiment, electronic storage 28 stores a plurality of different predetermined light therapy algorithms, and the subject (and/or a caregiver) select the predetermined light therapy algorithm that is appropriate for the subject via user interface 30.

As was mentioned above, in one embodiment, the predetermined light therapy algorithm may dictate the timing of the administration of radiation to the subject by sleep mask 10. As such, in this embodiment, processor 34 includes a clock. The clock may be capable of monitoring elapsed time from a given event and/or of monitoring the time of day. The subject (and/or a caregiver) may be enabled to correct the time of day generated by the clock of processor 34 via, for example, user interface 30.

One parameter of the predetermined light therapy algorithm is the magnitude of the intensity of the radiation. In one embodiment, processor 34 is configured to control first lighting module 16 and second lighting module 18 to adjust the intensity of the radiation provided to the subject such that the intensity of the radiation varies based on the output signals of one or more sensors 32. For example, in some instances, processor 34 may be configured to control first lighting module 16 and second lighting module 18 such that the radiation provided to the subject varies based on the current sleep stage of the subject. In such instances, processor 34 may be configured to first determine the sleep stage of the subject, or processor 34 may be configured to adjust the intensity of the radiation based on the one or more output signals from one or more sensors 32 without making a preliminary determination as to the sleep stage of the subject.

By way of non-limiting example, in one embodiment, processor 34 is configured to control first lighting module 16 and second lighting module 18 such that if the one or more output signals generated by one or more sensors 32 indicate that the subject is in a first, relatively deep, sleep stage, first lighting module 16 and second lighting module 18 provide radiation to the subject at a first intensity. However, if one or more output signals generated by one or more sensors 32 indicate that the subject is in a second, lighter, sleep stage, first lighting module 16 and second lighting module 18 are controlled to provide radiation to the subject at a second intensity that is lower than the first intensity. This may reduce the chance of the radiation waking the subject while the subject is in the second sleep stage. In one embodiment, the first sleep stage is non-REM sleep and the second sleep stage is REM sleep.

In one embodiment, processor 34 is configured to control first lighting module 16 and second lighting module 18 such that the intensity of the radiation provided to the subject does not rise above a threshold intensity. The threshold intensity varies based on the detected sleep stage of the subject. During deeper sleep, the threshold is increased as the subject is less likely to wake due to the radiation. During lighter sleep, the threshold is decreased, as the subject will be more likely to be awoken by the radiation.

In one embodiment, the threshold intensity is customized for the subject. For example, the subject may be able to adjust the threshold intensity via user interface 30. Adjustments by the subject to the threshold intensity may be made on a per sleep stage basis (e.g., adjusting the threshold intensity for REM sleep and non-REM sleep separately), or the subject may make a single adjustment to the threshold intensity that is implemented by processor 34 for across a plurality of sleep stages (e.g., across REM sleep and non-REM sleep). This may enable the subject to increase the threshold intensity if the radiation does not cause awakening, and to decrease the threshold intensity if the radiation is interfering with sleep.

In one embodiment, adjustments to the threshold intensity are made automatically. In this embodiment, as processor 34 monitors the wakefulness of the subject as the radiation is administered to the subject by first lighting module 16 and second lighting module 18. For example, in instances in which processor 34 determines information related to the sleep stages of the subject, this information may be monitored to determine if the subject is waking during the administration of radiation. If the information related to the sleep stages of the subject by processor 34 determines that the radiation is disrupting the sleep of the subject, processor 34 adjusts the threshold intensity to alleviate this disruption. This adjustment may be made by processor 34 on a per sleep stage basis, or as a single adjustment that is implemented for the intensity threshold across a plurality of sleep stages.

In one embodiment, processor 34 does not determine information related to the sleep stages of the subject, but does determine information related to the position of the eyelids of the subject, such as for example, whether the eyelids of the subject are open or closed (e.g., as described below). In this embodiment, the determination made by processor 34 related to the position of the eyelids of the subject may be used by processor 34 to determine wakefulness (e.g., the subject is determined to be awake if the eyelids open), and to adjust the threshold intensity of the therapy provided by sleep mask 10 if this monitoring of the wakefulness of the subject indicates that the therapy is interfering with sleep.

In one embodiment, adjustments made to the threshold intensity are made during a titration session in which processor 34 is capable of monitoring the sleep stages and/or wakefulness of the subject (e.g., in a clinical setting). These adjustments are then implemented in a less sophisticated embodiment of sleep mask 10 wherein processor 34 is not capable of monitoring the sleep stages and/or wakefulness of the subject. The adjustments may be communicated to the less sophisticated embodiment of sleep mask 10 via manual input, wireless communication, wired communication, removable electronic storage media, or otherwise communicated to sleep mask 10. In one embodiment, the less sophisticated embodiment of sleep mask 10 is capable of monitoring the sleep stages and/or wakefulness of the subject, but not with the same accuracy and/or precision that the more sophisticated embodiment of sleep mask 10 used in the titration session is capable of.

In one embodiment, to enhance the control of processor 34 over first lighting module 16 and second lighting module 18 in the delivery of light therapy to the subject, one or more sensors 32 include a sensor configured to generate an output signal that indicates core body temperature. By way of non-limiting example, sleep mask 10 may include one or two ear buds (not shown) that are configured to be placed in the ear canal of the subject. The ear bud may generate an output signal that conveys information related to the core body temperature of the subject. For instance, the output signal generated by the ear bud may vary as a function of the temperature within the ear canal and/or other parameters related to core body temperature.

The core body temperature of the subject will typically fluctuate with the sleep stages of the subject. Accordingly, by monitoring the output signal of the sensor configured to generate an output signal that indicates core body temperature, processor 34 may determine information related to the sleep stage of the subject. In one embodiment, the determination of core body temperature may be further implemented by processor 34 to diagnose one or more possible ailments of the subject. For example, patients suffering from Alzheimer's disease exhibit symptoms that are similar to those of fronto-temporal degeneration, particularly earlier on in the disease life cycle. However, research suggests that Alzheimer's patients experience a deregulation of Circadian rhythms that includes a maximum and/or minimum core body temperature that occur at times that are different from other individuals (e.g., delayed). In one embodiment, information related to core body temperature by processor 34 determined from output signals generated by one or more sensors 32 may be implemented to accurately diagnose Alzheimer's disease.

In one embodiment, one or more sensors 32 include an EEG sensor (not specifically shown) configured to generate one or more output signals that indicate electrical activity produced by the brain of the subject. The EEG sensor includes one or more electrodes that are applied to the head of the subject to receive electrical signals emitted by the subject's brain. The correlation between EEG output signals and sleep stages is known, and these understood relationships can be implemented by processor 34 to determine the sleep stage of the subject, transitions of the subject between sleep stages, and/or other information related to the sleeps stages of the subject. In some instances, the inclusion of an EEG sensor in one or more sensors 32 is made in a more sophisticated embodiment of sleep mask 10 that is implemented in a clinical setting to titrate one or more aspects of the light therapy provided by sleep mask 10 to the subject (e.g., as discussed above). However, this does not preclude the inclusion of EEG electrodes and/or EEG sensors in embodiments of sleep mask 10 that are produced for general consumer use.

Figure 5:
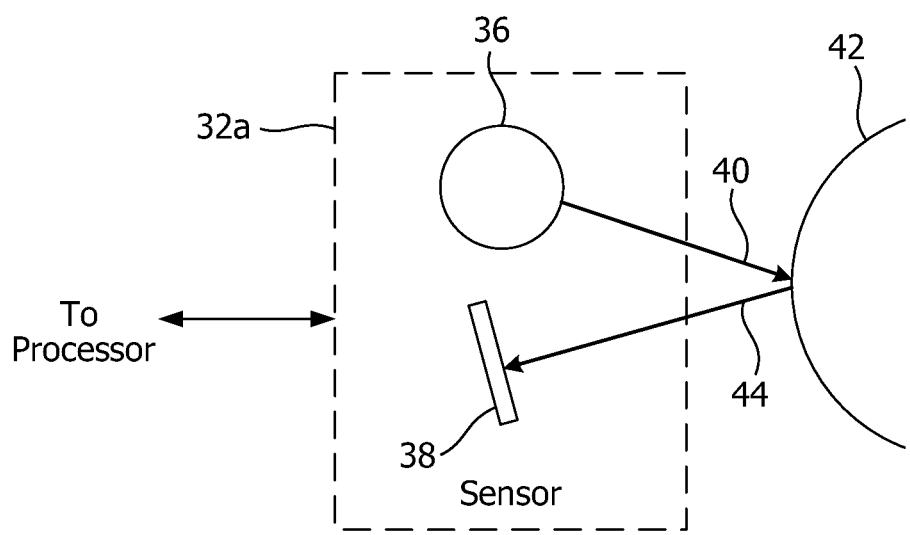
FIG. 5 illustrates a schematic representation of a sleep mask configured to provide light therapy to a subject, in accordance with one embodiment of the invention.

As was mentioned above, one or more sensors 32 may include a sensor configured to generate an output signal that indicates a distance between the sensor and the eye of the subject. FIG. 5 illustrates a schematic representation of an embodiment of a sensor 32a configured to generate such an output signal. In the embodiment illustrated in FIG. 5, sensor 32a includes an emitter 36 and a photosensitive detector 38.

Emitter 36 emits electromagnetic radiation 40 that is directed onto the eye 42 of the subject. Radiation 40 emitted by emitter 36 includes electromagnetic radiation having a wavelength (or wavelengths) and/or an intensity that does not adversely impact the eye 42 if the eye 42 is open. For example, in one embodiment, radiation 40 emitted by emitter 36 is in the infrared range, and is visually imperceptible to the eye 42. Emitter 36 may include one or more Organic Light Emitting Diodes ("OLEDs"), lasers (e.g., diode lasers or other laser sources), LEDs, directed ambient radiation, and/or other electromagnetic radiation sources. In one implementation, emitter 36 includes one or more infrared LEDs. While, the present invention is by no means limited to the use of LEDs, other advantages of implementing LEDs as emitter 36 include their light weight, compactness, low power consumption, low voltage requirements, low heat production, reliability, ruggedness, relatively low cost, and stability. Also they can be switched on and off very quickly, reliably, and reproducibly. In some instances, sensor 32a may include one or more optical elements (not shown) to guide, focus, and/or otherwise process radiation emitted by sensor 32a.

When emitter 36 emits radiation 40 at the eye 42, a portion of radiation 40 is reflected by the eye 42, and is returned to sensor 32a as radiation 44 in FIG. 5. Photosensitive detector 38 is disposed within sensor 32a to receive radiation 44 returning to sensor 32a from the eye 42. Photosensitive detector 38 is configured to generate an output signal based on one or more properties of radiation 44 (e.g., intensity, phase, angle of incidence to sensor 32a and/or photosensitive detector 38, a modulation, time of flight etc.). Due to the configuration of emitter 36 and/or photosensitive detector 38, one or more properties of radiation 44 upon which the output signal generated by photosensitive detector 38 is based convey information about the proximity of sensor 32a to the eye 42 (e.g., the distance between sensor 32a and the eye 42). In one embodiment, photosensitive detector 38 includes a PIN diode. In other embodiments, other photosensitive devices are employed as photosensitive detector 38. For instance, photosensitive detector 38 may take the form of a diode array, a CCD chip, a CMOS chip, a photo-multiplier tube and/or other photosensitive devices.

From the output signal generated by photosensitive detector 38 a processor (e.g., processor 34 shown in FIG. 4 and described above) may determine information about the sleep stage and/or wakefulness of the subject. For example, the distance from sensor 32a to the eye 42 will be different while the eyelid of the eye 42 is open than if the eyelid of the eye 42 is closed (due to the thickness of the eyelid tissue). Thus, the processor may determine whether the eye 42 is open or closed from the output signal generated by sensor 32a.

As was discussed above (with respect to FIG. 4), from an output signal conveying information related to whether the eyelid of the eye 42 is open or closed the processor can determine whether the subject is awake or asleep. From this information, the processor may adjust the light therapy that is administered by a sleep mask that includes sensor 32a (e.g., sleep mask 10). For example, a threshold intensity of the radiation provided to the eye 42 while the subject is asleep may be adjusted.

In one embodiment, the processor may implement one or more other/additional controls over the therapeutic radiation administered to the subject based on the output signal generated by sensor 32a. For example, if the subject opens the eye 42 during light therapy, a substantial amount of radiation may become incident on the opened eye. This may be uncomfortable for the subject, and may discourage use. In order to enhance the comfort of the subject, the processor may control the provision of therapeutic radiation to the eye 42 such that radiation is delivered at a first, relatively high, intensity if the output signal generated by sensor 32a is closed, and to deliver radiation at a second, relatively low intensity if the output signal generated by sensor 32a indicates that the eye 42 is open. In one embodiment, the second intensity may even be zero (or substantially zero), so that substantially no radiation is provided to the eye 42 of the subject while the eye 42 is open.

It will be appreciated that the disclosure of proximity sensor 32a provided in FIG. 5 and above is not intended to be limiting. Other types of proximity sensors capable of detecting a distance from the eye 42 may be employed without departing from the scope of this disclosure.

In one embodiment, the output signal generated by sensor 32a is implemented by the processor to determine information about the sleep stage of the subject. As the subject sleeps, the subject will pass back and forth between REM sleep and non-REM sleep. One of the physiological phenomena that characterizes REM sleep is a characteristic range of movements of the eyeball underneath the eyelid. By contrast, during non-REM sleep, the eyeball is relatively motionless. Other characteristics of eyeball movement may also be indicative of sleep state. For example, slow-rolling eye movements may occur around sleep onset.

The front of an eyeball is not a perfect arc. In particular, the cornea typically bulges out from the generally spherical shape of the eyeball. As such, during REM sleep, the proximity of the eye 42 to sensor 32a will vary as the cornea of the eye 42 passes below the point on the eyelid of the eye 42 that receives and reflects radiation 40. The output signal of sensor 32a reflects these proximity changes. Thus, the processor may be configured to determine information related to the sleep stage of the subject (e.g., whether the subject is in REM sleep or non-REM, whether the subject is experiencing or has experienced sleep onset, etc.) from the output signal generated by sensor 32a.

In one embodiment, sensor 32a includes a plurality of emitters and/or detectors that direct radiation to a plurality of locations on the eye 42. In this embodiment, the output signal generated by sensor 32a may not only provide information that indicates movement of the eyeball, but also the rotational position of the eyeball (based on the bulge of the cornea) and/or the time derivatives of position (e.g., velocity, acceleration, etc.). As an example, sensor 32a could be duplicated, and each of sensors could be mounted along a horizontal center plane on the mask to measure the distance to the eyelid or eyeball on either side of the vertical center plane toward each corner of at least one eye. This enables a continuous measure of the horizontal position of the cornea as the eye rotates. As an additional example, 3 or 4 sensors might be used positioned horizontally and vertically around and pointed toward a quadrant or similar zone of the eye, to enable continuous 2 dimensional rotation position and motion of the cornea above or beneath the eyelid.

Figure 6:
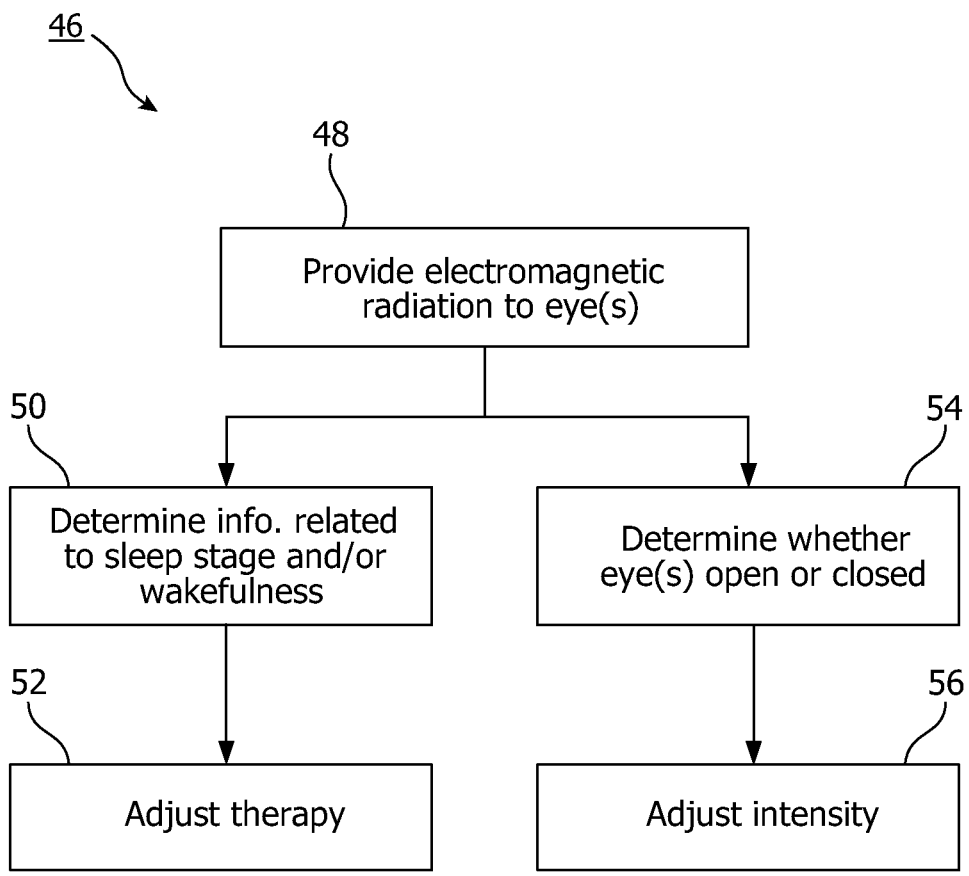
FIG. 6 illustrates a method of providing light therapy to a subject, according to one embodiment of the invention.

FIG. 6 illustrates a method 46 of providing light therapy to a subject. The operations of method 46 presented below are intended to be illustrative. In some embodiments, method 46 may be accomplished with one or more additional operations not described, and/or without one or more of the operations discussed. Additionally, the order in which the operations of method 46 are illustrated in FIG. 6 and described below is not intended to be limiting. In some embodiments, one or more of the method 46 may be implemented in a sleep mask that is the same as or similar to sleep mask 10 (shown in FIGS. 1-4, and described above). However, in some embodiments, method 46 is implemented in systems and/or contexts that are different than those described above with respect to sleep mask 10.

At an operation 48, light therapy radiation is provided to the eyes of the subject as the subject sleeps. The radiation is of an intensity and/or wavelength to have a therapeutic impact on the subject. In one embodiment, operation 48 is performed by one or more lighting modules that are similar to or the same as first lighting module 16 and/or second lighting module 18 (shown in FIGS. 3 and 4 and described above).

At an operation 50, information related to the sleep state of the subject is determined. The information related to the sleep state of the subject may include a determination of information related to current sleep stage of the subject and/or a determination as to whether the subject is asleep or awake. In one embodiment, operation 50 is performed by a processor that is similar to or the same as processor 34 (shown in FIG. 4 and described above) and/or the processor described above with respect to FIG. 5. The information determined at operation 50 may be determined based on one or more output signals that convey information related to the current sleep state of the subject. The one or more output signals may be generated by one or more sensors that are the same as or similar to one or more sensors 32 (shown in FIG. 4 and described above) and/or sensor 32a (shown in FIG. 5 and described above).

At an operation 52, one or more parameters of the light therapy radiation being delivered to the subject are adjusted based on the information determined at operation 50. The one or more parameters of the light therapy radiation that are adjusted may include an intensity of the radiation, a threshold intensity of the light therapy, and/or other parameters. In one embodiment, operation 52 is performed by a processor that is similar to or the same as processor 34 (shown in FIG. 4 and described above) and/or the processor described above with respect to FIG. 5.

At an operation 54, a determination is made as to whether the eyes of the subject are open or closed. In one embodiment, operation 54 is performed by a processor that is similar to or the same as processor 34 (shown in FIG. 4 and described above) and/or the processor described above with respect to FIG. 5. The determination made at operation 54 is made based on one or more output signals that convey information related to whether the eyes of the subject are open or closed. In one embodiment, the one or more output signals are generated by one or more sensors that are the same as or similar to one or more sensors 32 (shown in FIG. 4 and described above) and/or sensor 32a (shown in FIG. 5 and described above).

At an operation 56, the intensity of the light therapy radiation being delivered to the eyes of the subject is adjusted based on the determination made at operation 54. In particular, if the determination made at operation 54 is that the eyes of the subject are closed, the light therapy radiation may be delivered to the eyes of the subject at a first, relatively high, intensity. If the determination made at operation 56 is that the eyes of the subject are open, the light therapy radiation may be delivered to the eyes of the subject at a second, relatively low, intensity. In one embodiment, the second intensity is zero (e.g., substantially no radiation is provided to the eyes of the subject). Adjusting the intensity of the light therapy radiation from the first intensity to the second intensity may include one or more of powering down one or more radiation sources, filtering the light therapy radiation, blocking some or all of the light therapy radiation, reflecting some or all of the light therapy radiation, and/or implementing other techniques for reducing the intensity of the light therapy radiation. In one embodiment, operation 56 is performed by a processor controlling one or more lighting modules. The processor may be a processor that is similar to or the same as processor 34 (shown in FIG. 4 and described above) and/or the processor described above with respect to FIG. 5. The one or more lighting modules may include one or more lighting modules that are the same as or similar to first lighting module 16 and second lighting module 18 (shown in FIGS. 3 and 4 and described above).

Figure 7:
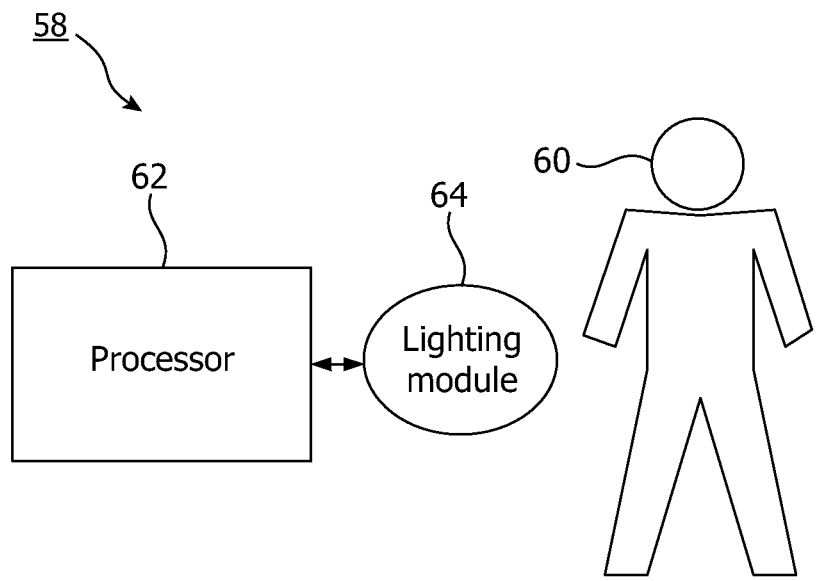
FIG. 7 illustrates a system configured to provide light therapy to a subject, according to one embodiment of the invention.

FIG. 7 illustrates a system 58 configured to provide light therapy to a subject 60. System 58 is configured to enhance the reception of the electromagnetic radiation provided to subject 60 during light therapy. In one embodiment, system 58 includes a lighting module 62 and a processor 64.

Lighting module 62 is configured to deliver electromagnetic radiation to the subject. In one embodiment, lighting module 62 includes one or both of first lighting module 16 and/or second lighting module 18 (shown in FIGS. 3 and 4 and described above). In one embodiment, lighting module 62 includes one or more radiation sources disposed within a light box device, or some other device configured to deliver radiation to subject 60 for light therapy purposes. In one embodiment, lighting module 62 is configured to dynamically adjust the wavelength of electromagnetic radiation delivered to subject 60. This may include selectively filtering radiation emitted by one or more sources, powering up or down radiation sources that emit light at different wavelengths, and/or other techniques for dynamically adjusting the wavelength of generated electromagnetic radiation.

Processor 64 is configured to provide information processing and/or system control capabilities in system 58. As such, processor 64 may include one or more of a digital processor, an analog processor, a digital circuit designed to process information, an analog circuit designed to process information, a state machine, and/or other mechanisms for electronically processing information. In order to provide the functionality attributed to processor 64 herein, processor 64 may execute one or more modules. The one or more modules may be implemented in software; hardware; firmware; some combination of software, hardware, and/or firmware; and/or otherwise implemented. In one embodiment, processor 64 is configured to control lighting module 62 to adjust the intensity and/or wavelength of the electromagnetic radiation that is delivered to subject 60 during light therapy.

During light therapy, in order for subject 60 to receive the therapeutic benefit of electromagnetic radiation provided to subject 60, photoreceptors on subject 60 must phototransduce the received photons of light. However, research has shown that at least in some cases the photoreceptors of a subject adapt over the course of a light therapy session (or a series of sessions), and begin to phototransduce less and less of the therapeutic light.

To address the adaptation of photoreceptors over time, some light therapy systems are configured to increase the intensity of the therapeutic electromagnetic radiation provided to the subject slowly over time. Other systems address adaptation by modulating the intensity of the delivered radiation up and down during individual therapy sessions. Both of these solutions are found to be uncomfortable by some subjects, which may lead to discontinuation of light therapy. In order to reduce the adaptation of the photoreceptors of subject 60 over time, processor 64 is configured to control lighting module 62 to modulate the wavelength of radiation delivered to subject 60 during light therapy.

Generally, the therapeutic benefits of light therapy are generated by providing electromagnetic radiation to subject 60 in the visible spectrum with a wave length below a therapeutic threshold. In one embodiment, the therapeutic spectrum is about 580 nm. During light therapy, processor 64 controls lighting module 62 to deliver radiation to subject 60 that includes a first portion of visible radiation and a second portion of visible radiation. The first portion of visible radiation is the portion of the radiation directed to subject 60 having wavelengths that are less than the therapeutic threshold. The second portion of visible radiation is the portion of the radiation directed to subject 60 having wavelengths that are greater than the therapeutic threshold. Rather than varying the overall intensity of the electromagnetic radiation that is delivered to subject 60, processor 64 controls lighting module 62 such that the intensities of the first portion of visible radiation and the second portion of visible radiation are varied, but the overall intensity of the visible radiation remains relatively fixed. This modulation of the intensities of the first and second portions of the visible radiation may provide some of the same benefits as simply varying the total intensity of the delivered radiation without the discomfort to subject 60 associated with the fluctuating total intensity.

Figure 8:
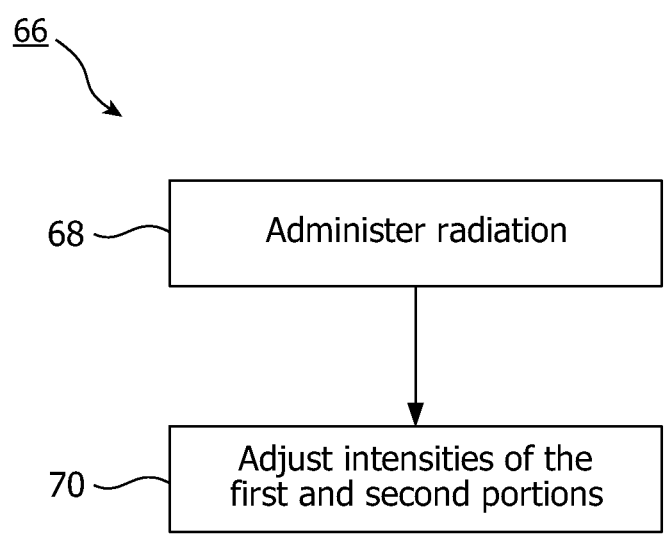
FIG. 8 illustrates a method of providing light therapy to a subject, according to one embodiment of the invention.

FIG. 8 illustrates a method 66 of providing light therapy to a subject. The operations of method 66 presented below are intended to be illustrative. In some embodiments, method 66 may be accomplished with one or more additional operations not described, and/or without one or more of the operations discussed. Additionally, the order in which the operations of method 46 are illustrated in FIG. 8 and described below is not intended to be limiting. In some embodiments, one or more of the method 66 may be implemented in a sleep mask that is the same as or similar to system 58 (shown in FIG. 7, and described above). However, in some embodiments, method 66 is implemented in systems and/or contexts that are different than those described above with respect to system 58.

At an operation 68, visible radiation is administered to the subject. The visible radiation includes a first portion of the visible radiation and a second portion of the visible radiation. The first portion of the visible radiation has wavelengths that fall within a first section of the visible spectrum. The second portion of the visible radiation has wavelengths that fall within a second section of the visible spectrum. In one embodiment, the first section of the visible spectrum is separated from the second section of the visible spectrum by a therapeutic threshold. In one embodiment, operation 68 is performed by one or more lighting modules that are the same as or similar to lighting module 62 (shown in FIG. 7 and described above).

At an operation 70, the intensity of the first portion of visible radiation and the intensity of the second portion of visible radiation are varied, or modulated, over time such that the overall intensity of the administered visible radiation remains relatively fixed. In one embodiment, operation 70 is performed by a processor that is the same as or similar to processor 64 (shown in FIG. 7 and described above) controlling one or more lighting modules that are the same as or similar to lighting module 62 (shown in FIG. 7 and described above).

It will be appreciated that the foregoing embodiments may be implemented to provide light therapy to a subject in an enhanced manner. In particular, the features of the invention disclosed herein may enhance the effectiveness of light therapy, the convenience of light therapy to the subject, the comfort of light therapy, and/or other aspects of light therapy.

Light therapy is known to regulate various substances within the human body. These substances include, for example, Melatonin and Luteinizing Hormone. As such, implementation of the features described herein in a method of treating a subject to regulate a level of Melatonin and/or Luteinizing Hormone in a therapeutic manner may provide an enhanced treatment of a Melatonin and/or Luteinizing mediated condition in that the treatment may be more effective, more convenient to the subject, more comfortable for the subject, and/or otherwise enhanced for the subject. By way of non-limiting example, regulating Melatonin levels is known to be a treatment for seizures, fibromyalgia, seasonal affective disorder, bipolar disorder, unipolar depression, bulimia, anorexia, schizophrenia, panic disorder, obsessive compulsive disorder, and/or other conditions and/or ailments. By way of further non-limiting example, regulating Luteinizing Hormone levels is known to be a treatment for irregular menstruation, irregular ovulation, lack of sex drive, muscle mass loss, other effects of aging, and/or other ailments and/or conditions.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to provide light therapy to a subject as the subject sleeps, the system comprising:
   one or more lighting modules configured to provide visible light to the eyes of the subject,
   one or more sensors configured to generate one or more output signals that convey information about the current sleep stage of the subject; and
   a processor configured to control the one or more lighting modules such that the one or more lighting modules provide visible light to the eyes of the subject,
   wherein the processor causes the intensity of the visible light provided to the eyes of the subject by the one or more lighting modules to vary based on the one or more output signals that convey information about the current sleep stage of the subject,
   wherein the processor controls the one or more lighting modules such that the one or more lighting modules provide visible light at (i) a first intensity if the one or more output signals indicate that the subject is experiencing REM sleep, and (ii) a second intensity if the one or more output signals indicate that the subject is experiencing non-REM deep sleep, and
   wherein the first intensity is less than the second intensity.

2. The system of claim 1, wherein the one or more sensors comprise a sensor configured to generate output signals that indicate a distance between the eye of the subject and the sensor.

3. The system of claim 1, wherein the one or more sensors comprise a sensor configured to generate output signals that indicate a core body temperature.

4. The system of claim 1, wherein the one or more sensors comprises an EEG sensor.

5. A method of providing light therapy to a subject as the subject sleeps, the method comprising:
   providing visible light to the eyes of the subject;
   determining the current sleep stage of the subject; and
   adjusting the intensity of the visible light directed to the eyes of the subject based on the current sleep stage of the subject, wherein adjusting the intensity of the visible light directed to the eyes of the subject based on the current sleep stage of the subject comprises (i) adjusting the intensity of the visible light to a first intensity if the subject is experiencing REM sleep, and (ii) adjusting the intensity of the visible light to a second intensity if the subject is experiencing non-REM deep sleep, and wherein the first intensity is less than the second intensity.

6. The method of claim 5, further comprising generating an output signal that indicates a distance between the eye of the subject and the sensor, wherein determining the current sleep stage of the subject comprises determining the current sleep stage of the subject based on the generated output signal.

7. The method of claim 5, further comprising generating output signals that indicate a core body temperature, wherein determining the current sleep stage of the subject comprises determining the current sleep stage of the subject based on the generated output signals.

8. The method of claim 5, further comprising generating one or more output signals that indicate electrical activity produced by the brain of the subject, wherein determining the current sleep stage of the subject comprises determining the current sleep stage of the subject based on the generated output signal.

9. A system configured to provide light therapy to a subject as the subject sleeps, the system comprising:
   means for providing visible light to the eyes of the subject;
   means for determining the current sleep stage of the subject; and
   means for adjusting the intensity of the visible light directed to the eyes of the subject based on the current sleep stage of the subject, wherein the means for adjusting the intensity of the visible light directed to the eyes of the subject based on the current sleep stage of the subject comprises (i) means for adjusting the intensity of the visible light to a first intensity if the subject is experiencing REM sleep, and (ii) means for adjusting the intensity of the visible light to a second intensity if the subject is experiencing non-REM deep sleep, and wherein the first intensity is less than the second intensity.

10. The system of claim 9, further comprising means for generating output signals that indicate a distance between the eye of the subject and the sensor, wherein the means for determining the current sleep stage of the subject comprises means for determining the current sleep stage of the subject based on the generated output signals.

11. The system of claim 9, further comprising means for generating output signals that indicate a core body temperature, wherein the means for determining the current sleep stage of the subject comprises means for determining the current sleep stage of the subject based on the generated output signals.

12. The system of claim 9, further comprising means for generating one or more output signals that indicate electrical activity produced by the brain of the subject, wherein the means for determining the current sleep stage of the subject comprises means for determining the current sleep stage of the subject based on the generated output signal.

* * * * *